United States Patent
Seo et al.

(10) Patent No.: US 9,513,269 B2
(45) Date of Patent: Dec. 6, 2016

(54) DISPLAY DEVICE

(71) Applicant: SAMSUNG DISPLAY CO., LTD., Yongin-si, Gyeonggi-do (KR)

(72) Inventors: Won-Kyoung Seo, Seoul (KR); Chung-Gwan Lee, Seoul (KR); Chung-Min Lee, Seoul (KR)

(73) Assignee: Samsung Display Co., Ltd. (KR)

( * ) Notice: Subject to any disclaimer, the term of this patent is extended or adjusted under 35 U.S.C. 154(b) by 87 days.

(21) Appl. No.: 14/463,544

(22) Filed: Aug. 19, 2014

(65) Prior Publication Data

US 2015/0285774 A1 Oct. 8, 2015

(30) Foreign Application Priority Data

Apr. 8, 2014 (KR) .................. 10-2014-0041719

(51) Int. Cl.
*G08B 21/00* (2006.01)
*G01N 33/02* (2006.01)
*B65D 79/02* (2006.01)
*B65D 51/24* (2006.01)

(52) U.S. Cl.
CPC ............ *G01N 33/02* (2013.01); *B65D 51/248* (2013.01); *B65D 79/02* (2013.01)

(58) Field of Classification Search
CPC ....... G01N 33/02; B65D 79/02; B65D 51/248; G08B 5/36; G08B 21/02; G08B 21/18; Y10T 29/49018; Y10T 436/2575; F25D 2700/08
USPC ............. 340/573.1, 540, 545.6, 309.16, 691.6,340/584; 368/10, 107; 422/404, 405; 426/87, 426/383; 206/459.1
See application file for complete search history.

(56) References Cited

U.S. PATENT DOCUMENTS

| 4,292,916 A * | 10/1981 | Bradley | G01K 3/04 116/205 |
| 6,230,919 B1 * | 5/2001 | Guillin | B65D 15/22 206/434 |
| 7,212,955 B2 * | 5/2007 | Kirshenbaum | G07C 1/00 340/540 |
| 8,138,939 B2 * | 3/2012 | Manning | A61J 7/0409 340/309.16 |
| 2004/0081023 A1 * | 4/2004 | Ho | A61J 7/0481 368/10 |
| 2006/0181961 A1 * | 8/2006 | Hobkirk | G04B 47/02 368/10 |
| 2010/0102959 A1 * | 4/2010 | Ashrafzadeh | G06Q 10/087 340/540 |
| 2011/0050415 A1 * | 3/2011 | Fan | B65D 43/16 340/540 |
| 2011/0057918 A1 * | 3/2011 | Kimura | G09G 3/3648 345/211 |

FOREIGN PATENT DOCUMENTS

| KR | 10-2008-0073227 | 8/2008 |
| KR | 10-2010-0004857 | 1/2010 |
| KR | 20-2010-0004857 | 5/2010 |
| KR | 10-2012-0086852 | 8/2012 |

* cited by examiner

*Primary Examiner* — Anh V La
(74) *Attorney, Agent, or Firm* — Innovation Counsel LLP

(57) ABSTRACT

A display device on a container cover includes a substrate, a driving circuit unit on the substrate, a display element unit on the driving circuit unit, a sealing member on the display element unit, and a coupling portion to a container body.

13 Claims, 5 Drawing Sheets

DISPLAY DEVICE

CROSS-REFERENCE TO RELATED APPLICATION

This application claims priority to and the benefit of Korean Patent Application No. 10-2014-0041719, filed on Apr. 8, 2014, in the Korean Intellectual Property Office, the disclosure of which application is incorporated herein in its entirety by reference.

BACKGROUND

1. Field

Present inventive concept relates to a display device on a container, and more particularly to a display device on a container cover capable of displaying a variety of information about contents in a container body.

2. Description of Related Technology

Various types of display devices have been increasingly used with the development of electronic technology. Especially, transparent display devices display letters or images while retaining visual transparency. The transparent display devices are generally manufactured by using a transparent electronic device made of a transparent material on a transparent substrate such as glass or plastic. The transparent display devices can be utilized in many different environments for various purposes, and can be applied to, for example, windows of homes and shops or windshields of a car or other vehicle so as to provide users with desired information. The transparent display devices in the windows of shops may be used for advertising and promotion.

Food is usually stored in a container body having a container cover at room temperature or under refrigeration. A conventional container does not have a means to display information about food, and thus information regarding how long the food is stored, environmental conditions under which the food is stored, and freshness of the food cannot be obtained from the conventional container.

It is to be understood that this background of the technology section is intended to provide useful background for understanding the here disclosed technology and as such, the technology background section may include ideas, concepts or recognitions that were not part of what was known or appreciated by those skilled in the pertinent art prior to corresponding effective filing dates of subject matter disclosed herein.

SUMMARY

The present inventive concept is directed to a display device on a container that is capable of displaying information about contents in a container body.

According to an embodiment, a display device on a container includes: a substrate; a driving circuit unit on the substrate; a display element unit on the driving circuit unit; a sealing member on the display element unit; and a coupling portion coupled to a container body.

The display device on a container cover may further include a sensing unit configured to measure at least one of temperature and humidity in the container body.

The display device on a container cover may display a state of contents assumed by using at least one piece of information about contents of the container body, a storage period, and temperature and humidity measured by the sensing unit.

The assumed state of contents may be freshness when the contents of the container body is food.

The freshness may be represented by a predetermined color.

The display device with a container cover may display the at least one piece of information about contents of the container body, a storage period, and temperature and humidity measured by the sensing unit.

The display device with a container cover may display a memo input by a user.

The display device with a container cover may further include a coating layer on the substrate.

The coating layer may include at least one of a waterproof coating layer and a heat-proof coating layer.

The display device with a container cover may further include a touch screen panel on the substrate.

The substrate and the sealing member may include any one of glass and transparent plastic.

The transparent plastic may include any one material selected from the group consisting of Kapton®, polyethersulphone (PES), polycarbonate (PC), polyimide (PI), polyethyleneterephthalate (PET), polyethylenenaphthalate (PEN), polyacrylate (PAR), and fiber reinforced plastic (FRP).

The driving circuit unit may include a thin film transistor layer.

The thin film transistor layer may include an oxide semiconductor.

The thin film transistor layer may include a transparent electrode material.

The transparent electrode material may include a transparent conducting oxide (TCO).

The transparent conducting oxide may include at least one oxide selected from the group consisting of indium tin oxide (ITO), indium zinc oxide (IZO), antimony tin oxide (ATO), aluminum zinc oxide (AZO), zinc oxide (ZnO), and mixtures thereof.

According to an embodiment, a container having a display device includes: a container body; a container cover including a coupling portion configured to couple the container body with the container cover; and a display device on the container cover, wherein the display device comprises a substrate;a driving circuit unit on the substrate; a display element unit on the driving circuit unit; and a sealing member on the display element unit.

The display device may be disposed on the coupling portion.

The display device may be disposed on a side surface of the container body.

According to embodiments of the inventive concept, a display device on a container is capable of displaying information regarding contents of a container body.

Further, according to embodiments of the inventive concept, a display device on a container is capable of displaying information about the kind of contents of a container body, a storage date, a storage period, a storage state, and the like.

The foregoing is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The above and other features and aspects of the present inventive concept will be more clearly understood from the following detailed description taken in conjunction with the accompanying drawings, in which.

DETAILED DESCRIPTION

Figure 1:
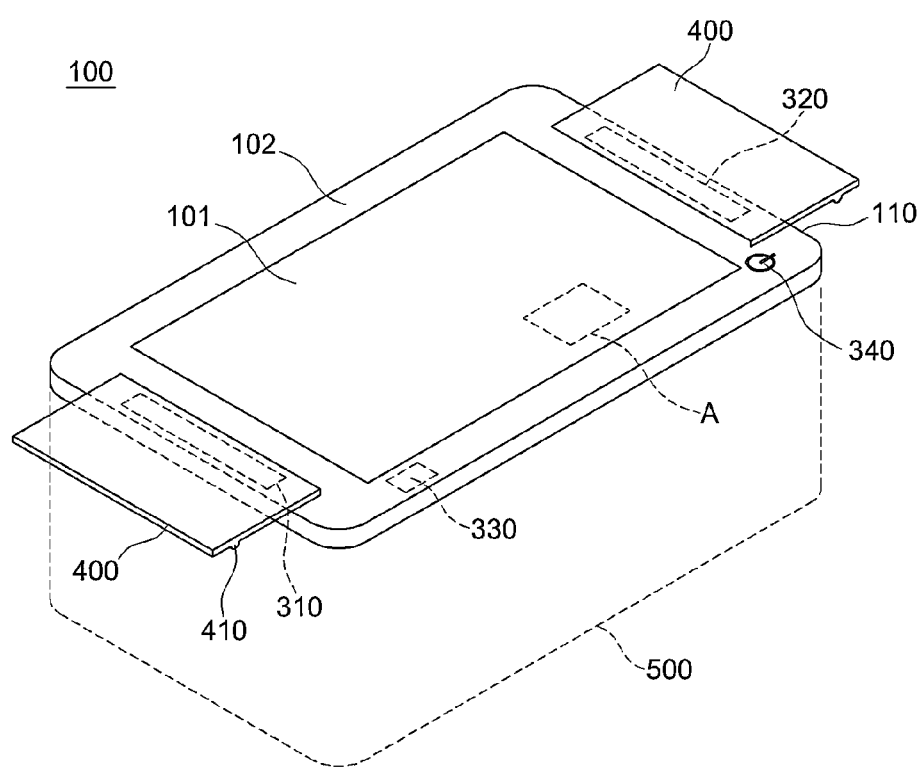
FIG. 1 is a schematic perspective view illustrating a display device on a container according to an embodiment of the present inventive concept.

Hereinafter, embodiments of the inventive concept are described with reference to the accompanying drawings.

Example embodiments of the inventive concept are illustrated in the accompanying drawings and described in the specification. The scope of the inventive concept is not limited to the example embodiments and should be construed as including all potential changes, equivalents, and substitutions to the example embodiments.

In the specification, when a first element is referred to as being "connected" to a second element, the first element may be directly connected to the second element or indirectly connected to the second element with one or more intervening elements interposed therebetween. The terms "comprises," "comprising," "includes," and/or "including," when used in this specification, may specify the presence of stated features, integers, steps, operations, elements, and/or components, but do not preclude the presence or addition of one or more other features, integers, steps, operations, elements, and/or components.

Although the terms "first," "second," and "third" and the like may be used herein to describe various elements, these elements should not be limited by these terms. These terms may be used to distinguish one element from another element. Thus, "a first element" could be termed "a second element" or "a third element," and "a second element" and "a third element" can be termed likewise without departing from the teachings herein. The description of an element as a "first" element may not require or imply the presence of a second element or other elements. The terms "first," "second," etc. may also be used herein to differentiate different categories or sets of elements. For conciseness, the terms "first," "second," etc. may represent "first-type (or first-set)," "second-type (or second-set)," etc., respectively.

Like reference numerals may refer to like elements in the specification.

FIG. 1 is a schematic perspective view illustrating a display device on a container according to an embodiment of the present inventive concept.

Referring to FIG. 1, the display device 100 on a container according to an embodiment of the present inventive concept includes a substrate 110 having a display area 101 and a non-display area 102. The display device 100 is disposed on a top surface of a container cover according to the embodiment of the present inventive concept. However, the location is not limited to the top surface of the container cover and may be disposed on a coupling portion 400 or on a side surface of the container body 500.

The display area 101 may include a plurality of pixels and may display an image using the pixels. The non-display area 102 may include a driver 310 configured to supply drive signals to each pixel, a power supply unit 320 configured to supply drive voltage to each pixel, a sensing unit 330 configured to measure temperature, humidity, and the like, and lines (not shown) configured for connection thereof. However, the display area 101, the driver 310, the power supply unit 320, and the sensing unit 330 may be accommodated in a coupling portion 400 that will be described below. A power supply button 340 may be disposed in the non-display area 102 so as to allow the display area 101 to operate. Alternatively, the display area 101, the driver 310, the power supply unit 320, and the sensing unit 330 may be accommodated in a side surface of the container body 500. The display area 101 on the coupling portion 400 or the side surface of the container body 500 enables easy recognition of the information in the display area when the containers having the display are piled one over another.

The display device 100 on a container cover according to one embodiment further includes the coupling portion 400 configured to be coupled to a container body 500 of which an upper surface is open. The container body may have a bottom surface and side surfaces extending substantially perpendicular to the bottom surface.

The coupling portion 400 may be positioned around the substrate 110. In FIG. 1, the coupling portion 400 may be disposed on two opposite sides of the substrate 110, but embodiments of the present disclosure are not limited thereto. The coupling portion 400 may be disposed on one side to four sides of the substrate 110. The coupling portions 400 may also be disposed on one side of the substrate 110.

The substrate 110 may be physically coupled to the container body 500 by utilizing the coupling portion 400. For instance, a wing protrusion 410 on the coupling portion 400 may be coupled to a locking protrusion (not shown) disposed on the side surface of the container body 500 so that the substrate 110 may be coupled to the container body 500. In addition, coupling methods generally used in the art may also be applied to embodiments of the present disclosure.

According to another embodiment, components such as the driver 310 and the power supply unit 320 may not be disposed on the coupling portion 400.

The sensing unit 330 may include a plurality of sensors configured to measure temperature, humidity, gas including volatile fatty acid such as acetic acid, propionic acid, butyric acid and etc) from rotten food and the like. The sensing unit 330 may be disposed in the form of a microchip on one surface of the substrate 110. The sensing unit 330 may be desirably disposed on one surface of the substrate 110 facing the container body 500. That is, when the container body 500 is coupled to the display device 100 with a container cover, the sensing unit 330 may measure temperature and humidity in the container body 500. The temperature and humidity measured by the sensing unit 330 may be transmitted to the driver 310 and may be displayed in the display area 101. A detailed example of the sensing unit 330 will be provided below.

The substrate 110 may have the same shape and area as those of the open upper surface of the container body 500. As illustrated in FIG. 1, the substrate 110 may be quadrangular in shape because the open upper surface of the container body 500 has a quadrangular shape. In other words, when the open upper surface of the container body 500 has a circular or oval shape, the substrate 110 may also have the circular or oval shape having the same area as the open upper surface of the container body 500. Although not illustrated in FIG. 1, a rubber packing may be further disposed around the substrate 110 so as to tightly couple the substrate 110 to the container body 500. The container body 500 may be made of any one of glass, ceramic, and plastic.

Figure 2:
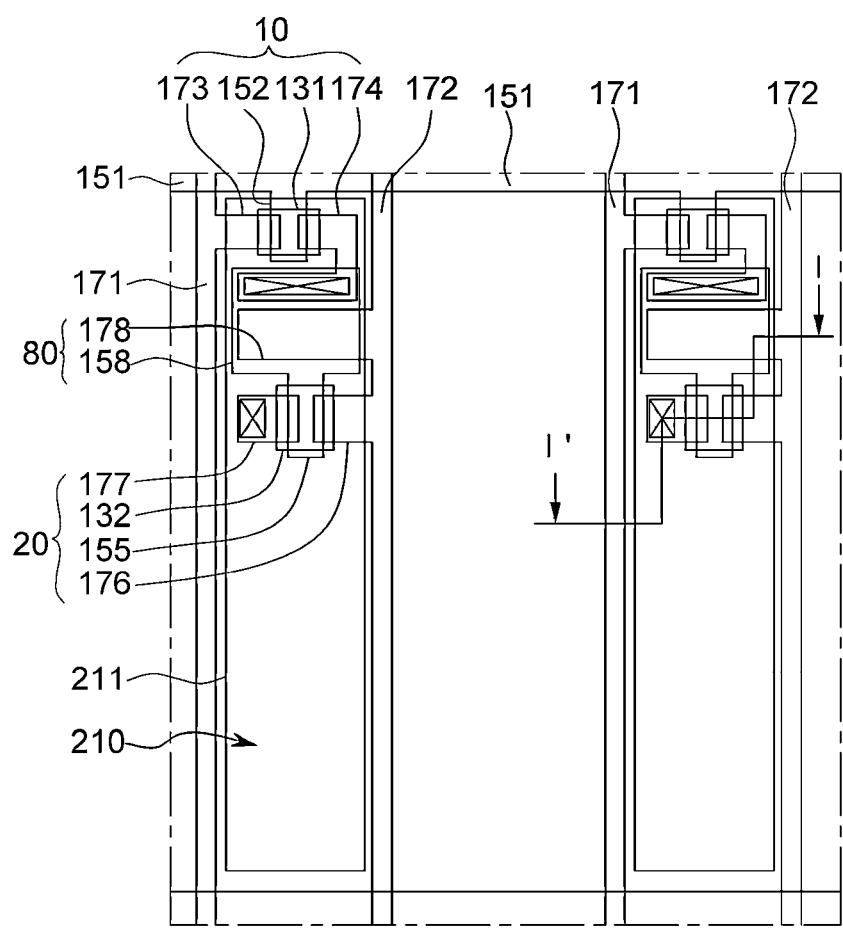
FIG. 2 is a partially enlarged view of part "A" of FIG. 1.
Figure 3:
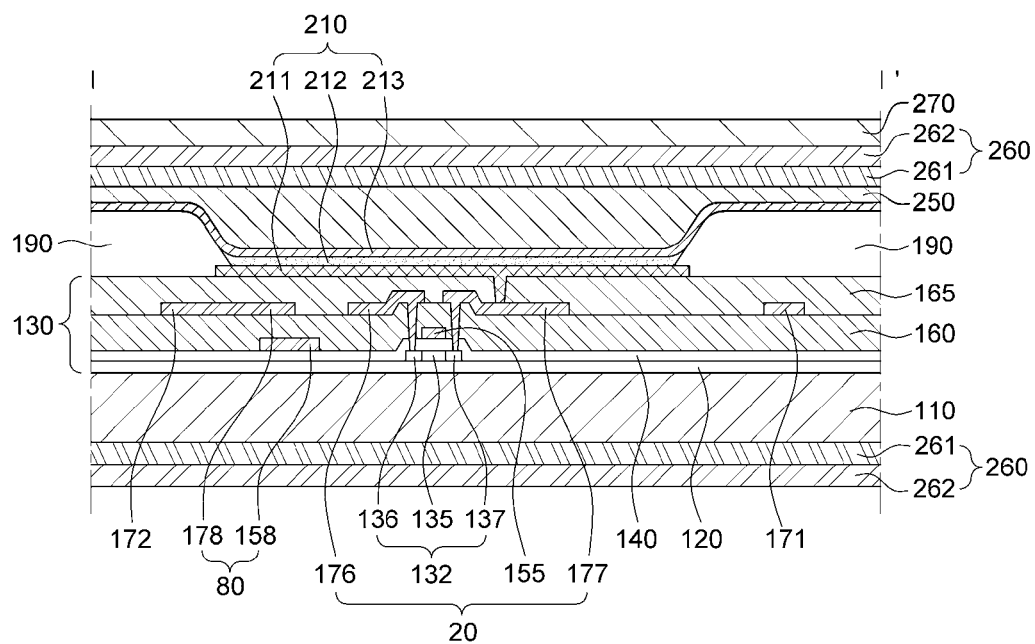
FIG. 3 is a cross-sectional view taken along line I-I' of FIG. 2.

FIG. 2 is a partially enlarged view of part "A" of FIG. 1.
FIG. 3 is a cross-sectional view taken along line I-I' of FIG. 2.

Referring to FIGS. 2 and 3, the display device 100 on a container cover according to one embodiment includes the substrate 110, a driving circuit unit 130 on the substrate 110, a display element unit 210 on the driving circuit unit 130, and a sealing member 250 on the display element unit 210.

A coating layer 260 may be disposed on one surface of the substrate 110 and one surface of the sealing member 250. The coating layer 260 may include at least one of a waterproof coating layer and a heat-proof coating layer.

A touch screen panel 270 may be disposed on the coating layer 260.

The display element unit 210 may be any one of an organic light emitting diode (OLED), a liquid crystal display (LCD), and an electrophoretic display (EPD). Such display elements may include in common a thin film transistor (TFT). Hereinafter, the display element unit 210 including an OLED will be described.

The driving circuit unit 130 may be disposed on the substrate 110 so as to drive the display element unit 210. The driving circuit unit 130 may include a switching TFT 10, a driving TFT 20, and a capacitor 80, and may drive the OLED 210 serving as a display element.

Although the detailed structures of the driving circuit unit 130 and the OLED 210 are illustrated in FIGS. 2 and 3, embodiments of the inventive concept are not limited to FIGS. 2 and 3. The driving circuit unit 130 and the OLED 210 may be embodied in many different forms within a range in which those skilled in the art can easily excogitate.

In FIG. 2, one pixel may include two TFTs and a capacitor, but embodiments of the inventive concept are not limited thereto. One pixel may include three or more TFTs and two or more capacitors, and may further include signal lines. The display device 100 on a container cover according to one embodiment may have many different structures. Herein, the term "pixel" refers to the smallest unit for displaying an image.

Referring to FIGS. 2 and 3, every pixel may include a switching TFT 10, a driving TFT 20, a capacitor 80, and an OLED 210. The configuration including the switching TFT 10, the driving TFT 20, and the capacitor 80 is called the driving circuit unit 130.

The driving circuit unit 130 may further include a gate line 151 arranged along one direction, a data line 171 insulated from and intersecting (crossing) the gate line 151, and a common power supply line 172. One pixel is generally defined by the gate line 151, the data line 171, and the common power supply line 172, but may be defined differently. For example, the pixel area may be defined by a black matrix or a pixel defining layer (PDL).

The substrate 110 may be a transparent insulating substrate made of glass, transparent plastic, or the like. In one embodiment, the substrate 110 may be made of any one material selected from the group consisting of Kapton®, polyethersulphone (PES), polycarbonate (PC), polyimide (PI), polyethyleneterephthalate (PET), polyethylenenaphthalate (PEN), polyacrylate (PAR), and fiber reinforced plastic (FRP).

A buffer layer 120 may be disposed on the substrate 110. The buffer layer 120 may prevent infiltration of undesirable elements such as impurities and moisture, and may provide a planar surface. The buffer layer 120 may be made of a suitable material for planarizing and/or preventing infiltration. For example, the buffer layer 120 may include at least one selected from the group consisting of silicon nitride ($SiN_x$), silicon oxide ($SiO_2$), and silicon oxynitride ($SiO_xN_y$). In an implementation, the buffer layer 120 may be omitted depending on kinds and manufacturing process conditions of the substrate 110.

A switching semiconductor layer 131 and a driving semiconductor layer 132 may be disposed on the buffer layer 120. The switching and driving semiconductor layers 131 and 132 may include at least one of polycrystalline silicon, amorphous silicon, and oxide semiconductors such as indium gallium zinc oxide (IGZO) and indium zinc tin oxide (IZTO). For instance, when the driving semiconductor layer 132 illustrated in FIG. 3 is made of the polycrystalline silicon, the driving semiconductor layer 132 may include a channel area 135 that is not doped with impurities, and p+ doped source and drain areas 136 and 137 on the respective sides of the channel area 135. P-type impurities such as boron B may be used as dopant ions. $B_2H_6$ may be used to dope p+ doped source and drain areas 136 and 137. Such impurities may vary depending on the kinds of thin film transistors (TFTs). According to one embodiment, a PMOS-structured TFT using the p-type impurities is used as the driving TFT 20, but embodiments of the inventive concept are not limited thereto. An NMOS-structured TFT may also be used as the driving TFT 20. When using a plurality of driving TFT is used as a driving TFT, CMOS structured TFT may also be used as the driving TFT.

A gate insulating layer 140 may be disposed on the switching and driving semiconductor layers 131 and 132. The gate insulating layer 140 may include at least one selected from the group consisting of tetraethyl orthosilicate (TEOS), silicon nitride ($SiN_x$), and silicon oxide ($SiO_2$). For instance, the gate insulating layer 140 may have a double layer structure in which a silicon nitride layer having a thickness of about 40 nm and a TEOS layer having a thickness of about 80 nm are sequentially laminated, but the structure of the gate insulating layer 140 is not limited thereto.

A gate wire including gate electrodes 152 and 155 may be disposed on the gate insulating layer 140. The gate wire may further include a gate line 151, a first capacitor plate 158, and other lines. The gate electrodes 152 and 155 may be disposed to overlap at least a part of the semiconductor layers 131 and 132 and, for example, to overlap the channel area 135. The gate electrodes 152 and 155 may prevent the channel area 135 from being doped with impurities when the source and drain areas 136 and 137 of the semiconductor layers 131 and 132 are doped with the impurities.

The gate electrodes 152 and 155 and the first capacitor plate 158 may be disposed on the same plane and may be made of substantially the same metal material. The gate electrodes 152 and 155 and the first capacitor plate 158 may include at least one selected from the group consisting of molybdenum (Mo), chromium (Cr), and tungsten (W).

An interlayer insulating layer 160 configured to cover the gate electrodes 152 and 155 may be disposed on the gate insulating layer 140. The interlayer insulating layer 160 may be made of tetraethyl orthosilicate (TEOS), silicon nitride ($SiN_x$), or silicon oxide ($SiO_x$) similar to the gate insulating layer 140, but embodiments of the inventive concept are not limited thereto.

A data wire including source electrodes 173 and 176 and drain electrodes 174 and 177 may be disposed on the interlayer insulating layer 160. The data wire may further include a data line 171, a common power supply line 172, a second capacitor plate 178, and other lines. The source electrodes 173 and 176 and the drain electrodes 174 and 177 are respectively coupled to the source area 136 and the drain area 137 of the semiconductor layers 131 and 132 through contact openings formed in the gate insulating layer 140 and the interlayer insulating layer 160.

Thus, the switching TFT 10 may include the switching semiconductor layer 131, the switching gate electrode 152, the switching source electrode 173, and the switching drain electrode 174, and the driving TFT 20 may include the driving semiconductor layer 132, the driving gate electrode 155, the driving source electrode 176, and the driving drain electrode 177. The configurations of the TFTs 10 and 20 are not limited to the above-described embodiment and may vary according to known configurations that can be carried out by those skilled in the art.

The capacitor 80 may include the first capacitor plate 158 and the second capacitor plate 178 with the interlayer insulating layer 160 interposed therebetween.

The switching TFT 10 may function as a switching device which selects a pixel to perform light emission. The switching gate electrode 152 may be coupled to the gate line 151. The switching source electrode 173 may be coupled to the data line 171. The switching drain electrode 174 may be spaced apart from the switching source electrode 173 and coupled to the first capacitor plate 158.

The driving TFT 20 may apply driving power to a pixel electrode 211, which allows a light emitting layer 212 of the OLED 210 in the selected pixel to emit light. The driving gate electrode 155 may be coupled to the first capacitor plate 158. The driving source electrode 176 and the second capacitor plate 178 may be coupled to the common power supply line 172. The driving drain electrode 177 may be coupled to the pixel electrode 211 of the OLED 210 through a contact hole.

With the above-described structure, the switching TFT 10 may be operated by a gate voltage applied to the gate line 151, and may function to transmit a data voltage applied to the data line 171 to the driving TFT 20. A voltage equivalent to a differential between a common voltage applied to the driving TFT 20 from the common power supply line 172 and the data voltage transmitted from the switching TFT 10 may be stored in the capacitor 80, and a current corresponding to the voltage stored in the capacitor 80 may flow to the OLED 210 through the driving TFT 20, so that the OLED 210 may emit light.

A planarization layer 165 may be configured to cover the data wire patterned on the same plane as the data line 171, the common power supply line 172, the source electrodes 173 and 176, the drain electrodes 174 and 177, the second capacitor plate 178, and the like that are disposed on the interlayer insulating layer 160.

The planarization layer 165 may serve to planarize a surface of the OLED 210 by eliminating or reducing steps so as to increase light emission efficiency of the OLED 210 that will be disposed on the planarization layer 165. The planarization layer 165 may be made of at least one selected from the group consisting of a polyacrylate resin, an epoxy resin, a phenolic resin, a polyamide resin, a polyimide resin, an unsaturated polyester resin, a polyphenylenether resin, a polyphenylene sulfide resin, and benzocyclobutene (BCB).

The pixel electrode 211 of the OLED 210 may be disposed on the planarization layer 165. The pixel electrode 211 may be coupled to the drain electrode 177 through a contact opening of the planarization layer 165.

A pixel defining layer (PDL) 190 configured to define a pixel area by exposing at least a part of the pixel electrode 211 may be disposed on the planarization layer 165. That is, the pixel electrode 211 may be disposed to correspond to a pixel area defined by the PDL 190. The PDL 190 may be made of a polyacrylate resin or a polyimide resin.

The light emitting layer 212 may be disposed on the pixel electrode 211 in the pixel area and a common electrode 213 may be disposed on the PDL 190 and the light emitting layer 212. The light emitting layer 212 may include a low molecular weight organic material or a high molecular weight organic material. At least one of a hole injection layer (HIL) and a hole transport layer (HTL) may be disposed between the pixel electrode 211 and the light emitting layer 212, and at least one of an electron transport layer (ETL) and an electron injection layer (EIL) may be disposed between the light emitting layer 212 and the common electrode 213.

The pixel electrode 211 and the common electrode 213 may be any one of a transmissive electrode, a transflective electrode, and a reflective electrode.

A transparent conductive oxide (TCO) may be used to form the transmissive electrode. The TCO may include at least one selected from the group consisting of indium tin oxide (ITO), indium zinc oxide (IZO), antimony tin oxide (ATO), aluminum zinc oxide (AZO), zinc oxide (ZnO), and mixtures thereof.

A metal such as magnesium (Mg), silver (Ag), gold (Au), calcium (Ca), Lithium (Li), Chromium (Cr), aluminum (Al), and copper (Cu), or alloys thereof may be used to form the transflective electrode and the reflective electrode. In this case, the transflective electrode and the reflective electrode may be determined by thickness of the electrode. In general, the transflective electrode has a thickness of about 200 nm or less and the reflective electrode has a thickness of about 300 nm or greater. As the thickness of the transflective electrode becomes thinner, light transmittance increases, but resistance also increases. In contrast, as the thickness of the transflective electrode becomes thicker, light transmittance decreases.

The transflective electrode and the reflective electrode may have a multilayer structure that includes a metal layer made of a metal or an alloy thereof and a transparent conductive oxide layer laminated on the metal layer.

According to one embodiment, the display device 100 on a container cover may have a dual-side emission structure, and thus light may be emitted in directions of the pixel electrode 211 and the common electrode 213 so that an image is displayed. Therefore, the pixel electrode 211 and the common electrode 213 may be made of a transmissive or transflective electrode.

The sealing members 250 may be disposed on the common electrode 213. The sealing member 250 may be a transparent insulator made of glass or transparent plastic. The sealing member 250 may have a thin film encapsulation structure in which one or more inorganic layers and one or more organic layers are alternately laminated.

The coating layer 260 may be disposed on the substrate 110 and one surface of the sealing member 250. The coating layer 260 may include at least one selected from the group consisting of a water-proof coating layer 261 and a heat-proof coating layer 262. The coating layer 260 may prevent penetration of water or heat from contents of the container body 500 or surrounding environment, thereby reducing damage to the display device 100 on a container cover.

The water-proof coating layer 261 may be made of a polymer material that has transparency. The water-proof coating layer 261 may be made of, for example, polyester or parylene. The water-proof coating layer 261 may be coated by a thermal diffusion deposition method at room temperature or may be formed by bonding a film having water proof characteristic. In addition, water-proof coating materials generally used in the art may also be applied to embodiments of the inventive concept.

The heat-proof coating layer 262 may be made of materials that have transparency and high thermal conductivity. For example, the heat-proof coating layer 262 may be made of a graphite sheet or acrylic sheet. In addition, heat-proof coating materials generally used in the art may also be applied to embodiments of the inventive concept.

The touch screen panel 270 may be disposed on the coating layer 260. A user may select a mode or input letters by utilizing the touch screen panel 270.

Figure 4:
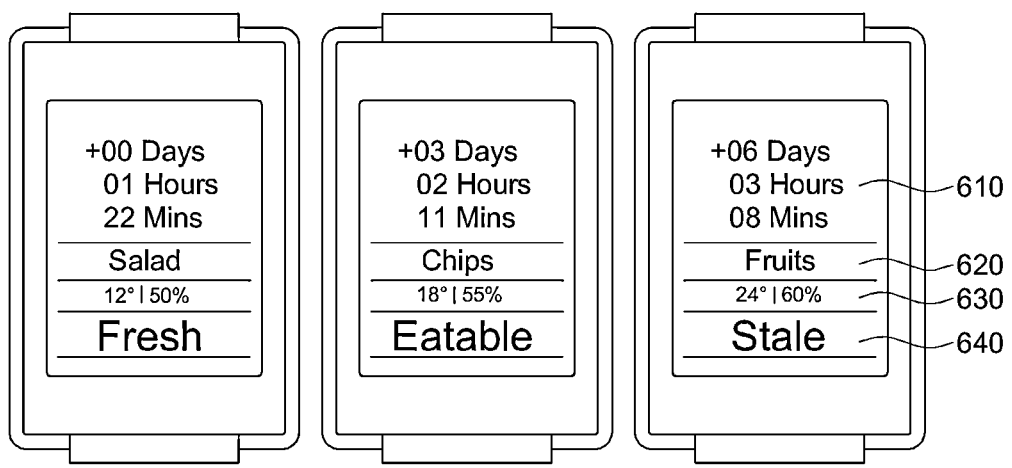
FIGS. 4 and 5 provide examples of application of a display device on a container according to an embodiment of the present inventive concept.
Figure 5:
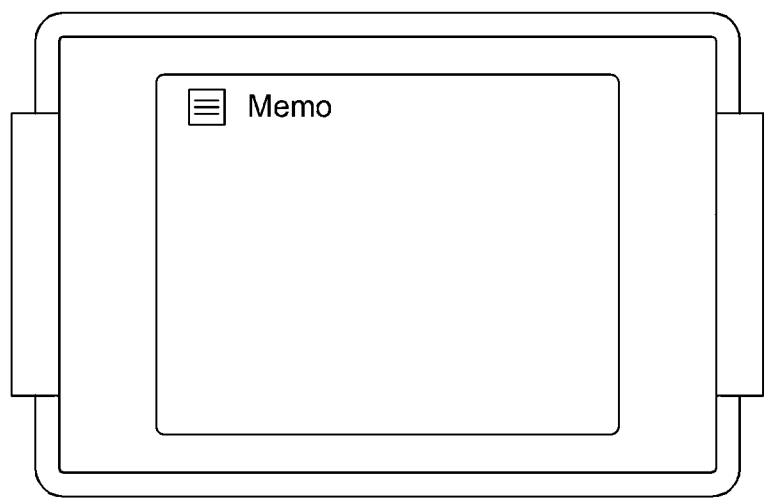

FIGS. 4 and 5 provide examples of application of a display device on a container cover according to an embodiment of the present inventive concept.

Referring to FIG. 4, the display device 100 on a container cover according to one embodiment may display storage period information 610 on how long contents are stored in a container body, contents information 620, temperature, humidity and gas information 630 measured by the sensing unit, and a current state 640 of the contents assumed from the information such as storage period information 610, temperature, humidity and gas information 630.

For instance, if the contents of the container body is food, the kind of the food may be registered by a user when it is initially stored, and from the point of time when the kind of the food is registered, a storage period of time may be measured and displayed. Further, temperature and humidity inside the container body and around the container body are continuously measured and displayed. Food freshness assumed from information of the kind of food, a storage period of time, a storage environment, gas generated from the food, and the like may also be displayed.

As illustrated in FIG. 4, information (e.g., fresh, eatable, or stale) may be displayed depending upon the freshness.

The information regarding the freshness, as described above, may be displayed in letters or in predetermined colors. In one embodiment, in the case when the food stored in the container is fresh, it may be displayed in green, in the case when the food stored in the container is eatable, it may be displayed in orange, and in the case when the food stored in the container is stale, it may be displayed in red. When the freshness information is displayed in a predetermined color, the user may easily ascertain the freshness of the foods in the container body.

This is for illustrative purposes only, and the information about the contents of the container body may be obviously displayed in a variety of methods.

Referring to FIG. 5, the display device 100 on a container cover according to one embodiment may display a memo input by a user in the display area thereof. The user may input the memo utilizing a stylus pen (not shown) or a touch keyboard.

From the foregoing, it will be appreciated that various embodiments in accordance with the present disclosure have been described herein for purposes of illustration, and that various modifications may be made without departing from the scope and spirit of the present teachings. Accordingly, the various embodiments disclosed herein are not intended to be limiting of the scope and spirit of the present inventive concept.

What is claimed is:

1. A display device on a container cover, comprising:
    a substrate;
    a driving circuit unit on the substrate;
    a display element unit on the driving circuit unit;
    a sealing member on the display element unit;
    a coupling portion coupled to a container body; and
    a sensing unit configured to measure at least one of temperature and humidity in the container body,
    wherein the display device displays a state of contents assumed by using at least one piece of information about contents in the container body, a storage period, temperature, humidity and gas measured by the sensing unit, and
    wherein the state of contents including freshness of food is represented by a predetermined color.

2. The display device on a container cover of claim 1, wherein the display device displays the at least one piece of information about contents of the container body, a storage period, temperature, humidity and gas measured by the sensing unit.

3. The display device on a container cover of claim 1, wherein the display device displays a memo input by a user.

4. The display device on a container cover of claim 1, further comprising a coating layer on the substrate.

5. The display device on a container cover of claim 4, wherein the coating layer comprises at least one of a water-proof coating layer and a heat-proof coating layer.

6. The display device on a container cover of claim 1, further comprising a touch screen panel on the substrate.

7. The display device on a container cover of claim 1, wherein the substrate and the sealing member comprise any one of glass and transparent plastic.

8. The display device on a container cover of claim 7, wherein the transparent plastic comprises any one material selected from the group consisting of Kapton®, polyethersulphone (PES), polycarbonate (PC), polyimide (PI), polyethyleneterephthalate (PET), polyethylenenaphthalate (PEN), polyacrylate (PAR), and fiber reinforced plastic (FRP).

9. The display device on a container cover of claim 1, wherein the driving circuit unit comprises a thin film transistor layer.

10. The display device on a container cover of claim 9, wherein the thin film transistor layer comprises an oxide semiconductor.

11. The display device on a container cover of claim 9, wherein the thin film transistor layer comprises a transparent electrode material.

12. The display device on a container cover of claim 11, wherein the transparent electrode material comprises a transparent conducting oxide (TCO).

13. The display device on a container cover of claim 12, wherein the transparent conducting oxide comprises at least one oxide selected from the group consisting of indium tin oxide (ITO), indium zinc oxide (IZO), antimony tin oxide (ATO), aluminum zinc oxide (AZO), zinc oxide (ZnO), and mixtures thereof.

* * * * *